United States Patent
Whyne et al.

(10) Patent No.: US 10,045,801 B2
(45) Date of Patent: Aug. 14, 2018

(54) BONE STABILIZATION DEVICE AND METHOD OF PRODUCTION

(71) Applicants: SUNNYBROOK HEALTH SCIENCES CENTRE, Toronto (CA); THE GOVERNING COUNCIL OF THE UNIVERSITY OF TORONTO, Toronto (CA)

(72) Inventors: Cari Marisa Whyne, Toronto (CA); Robert M. Pilliar, Toronto (CA); Jeffrey Allan Fialkov, Toronto (CA); Paul Santerre, Whitby (CA); Eran Regev, Har Gilo (IL)

(73) Assignees: The Governing Council of the University of Toronto, Toronto, ON (CA); Sunnybrook Health Sciences Centre, Toronto, ON (CA)

( * ) Notice: Subject to any disclaimer, the term of this patent is extended or adjusted under 35 U.S.C. 154(b) by 719 days.

(21) Appl. No.: 14/418,707

(22) PCT Filed: Jul. 22, 2013

(86) PCT No.: PCT/CA2013/050570
§ 371 (c)(1),
(2) Date: Jan. 30, 2015

(87) PCT Pub. No.: WO2014/019083
PCT Pub. Date: Feb. 6, 2014

(65) Prior Publication Data
US 2015/0202046 A1  Jul. 23, 2015

Related U.S. Application Data

(60) Provisional application No. 61/677,290, filed on Jul. 30, 2012.

(51) Int. Cl.
A61B 17/80    (2006.01)
B32B 13/12    (2006.01)
(Continued)

(52) U.S. Cl.
CPC ........... *A61B 17/80* (2013.01); *A61B 17/688* (2013.01); *A61F 2/28* (2013.01); *A61L 31/026* (2013.01);
(Continued)

(58) Field of Classification Search
CPC ............... A61B 17/688; A61B 17/80–17/8076
(Continued)

(56) References Cited

U.S. PATENT DOCUMENTS 6,066,176 A    5/2000   Oshida
6,486,232 B1   11/2002  Wise
(Continued)

FOREIGN PATENT DOCUMENTS

CA    2268478     2/1999
WO    2008080239  7/2008
WO    2012004570  1/2012

OTHER PUBLICATIONS

Pietrzak WS, Sarveer D., Verstynen M.; Bioresorbable Implants—Practical Considerations. Bone 1996; 19(1):109-119.
(Continued)

*Primary Examiner* — Eric S Gibson
(74) *Attorney, Agent, or Firm* — Lynn Schumacher; Hill & Schumacher

(57) ABSTRACT

The present disclosure discloses a bone stabilization device (also referred to as a bone tape), which includes a composite flexible construct including a rigidifiable biocompatible sheet structure having first and second opposed surfaces. A biocompatible cement is located on the first surface. In use the composite flexible construct is applied to a bone with the
(Continued)

cement contacted directly to the bone. The cement is made of a material that, once adhered to the bone, is curable to mechanically and/or ionically bond to the sheet structure and to chemically bond to the bone to achieve a permanent bond. The bone tape allows simultaneous alignment and stabilization of multiple articulated fragments for successful 3D reconstruction of shattered bones. Initial flexibility and translucency provided by the bone tape can facilitate the temporary stabilization and alignment adjustment of multiple fragments, prior to permanent rigid bonding.

20 Claims, 4 Drawing Sheets

(51) Int. Cl.
| A61L 31/08 | (2006.01) |
| A61L 31/10 | (2006.01) |
| A61L 31/12 | (2006.01) |
| A61L 31/14 | (2006.01) |
| A61B 17/68 | (2006.01) |
| A61F 2/28 | (2006.01) |
| A61L 31/02 | (2006.01) |
| B32B 5/02 | (2006.01) |
| B32B 13/14 | (2006.01) |
| B32B 21/08 | (2006.01) |
| B32B 21/10 | (2006.01) |
| B32B 21/14 | (2006.01) |
| B32B 27/20 | (2006.01) |
| B32B 27/28 | (2006.01) |
| B32B 27/34 | (2006.01) |
| B32B 27/36 | (2006.01) |
| B32B 27/40 | (2006.01) |
| A61B 17/00 | (2006.01) |

(52) U.S. Cl.
CPC .......... A61L 31/088 (2013.01); A61L 31/10 (2013.01); A61L 31/127 (2013.01); A61L 31/128 (2013.01); A61L 31/14 (2013.01); A61L 31/146 (2013.01); A61L 31/148 (2013.01); B32B 5/028 (2013.01); B32B 13/12 (2013.01); B32B 13/14 (2013.01); B32B 21/08 (2013.01); B32B 21/10 (2013.01); B32B 21/14 (2013.01); B32B 27/20 (2013.01); B32B 27/285 (2013.01); B32B 27/34 (2013.01); B32B 27/36 (2013.01); B32B 27/365 (2013.01); B32B 27/40 (2013.01); A61B 2017/00004 (2013.01); A61F 2210/0004 (2013.01); A61L 2430/02 (2013.01); B32B 2260/021 (2013.01); B32B 2260/046 (2013.01); B32B 2262/105 (2013.01); B32B 2307/542 (2013.01); B32B 2307/7163 (2013.01)

(58) Field of Classification Search
USPC .............. 606/70, 71, 280–299, 902–905
See application file for complete search history.

(56) References Cited

U.S. PATENT DOCUMENTS

| 7,066,962 | B2* | 6/2006 | Swords ............... A61F 2/0059 623/17.18 |
| 8,303,976 | B2* | 11/2012 | Sapieszko ........... C04B 38/0025 424/422 |
| 8,398,720 | B2 | 3/2013 | Swords et al. |
| 8,403,968 | B2* | 3/2013 | Rabiner ............. A61B 17/8085 606/192 |
| 8,431,226 | B2 | 4/2013 | Huerta et al. |
| 2003/0036800 | A1* | 2/2003 | Meredith ............. A61B 17/866 623/23.63 |
| 2003/0039676 | A1* | 2/2003 | Boyce ................ A61B 17/0401 424/423 |
| 2004/0039387 | A1* | 2/2004 | Gause ................ A61B 17/1728 606/86 B |
| 2004/0043051 | A1* | 3/2004 | Pilliar ..................... A61L 15/24 424/423 |
| 2004/0111089 | A1* | 6/2004 | Stevens ............. A61B 17/1728 606/86 B |
| 2007/0118129 | A1* | 5/2007 | Fraser ................... A61F 2/0811 606/71 |
| 2007/0123883 | A1* | 5/2007 | Ellis .................. A61B 17/8076 606/326 |
| 2007/0173949 | A1 | 7/2007 | Sharps et al. |
| 2007/0191963 | A1* | 8/2007 | Winterbottom ........... A61F 2/28 623/23.5 |
| 2007/0233272 | A1* | 10/2007 | Boyce ................ A61B 17/0401 623/23.63 |
| 2007/0270852 | A1* | 11/2007 | Tormala ................. A61B 17/80 606/281 |
| 2008/0051786 | A1* | 2/2008 | Jensen ............... A61B 17/8057 606/86 A |
| 2008/0077133 | A1* | 3/2008 | Schulze ............. A61B 17/8085 606/60 |
| 2008/0097432 | A1* | 4/2008 | Schulze ............. A61B 17/8085 606/86 A |
| 2008/0188945 | A1* | 8/2008 | Boyce ................ A61B 17/0401 623/23.61 |
| 2008/0269753 | A1* | 10/2008 | Cannestra .......... A61B 17/7059 606/70 |
| 2009/0088851 | A1* | 4/2009 | Melkent ................ A61F 2/4425 623/17.16 |
| 2010/0256641 | A1* | 10/2010 | Rabiner ............. A61B 17/8085 606/70 |
| 2011/0014244 | A1* | 1/2011 | Sapieszko ........... C04B 38/0025 424/400 |
| 2011/0137351 | A1* | 6/2011 | Huebner ............. A61B 17/1728 606/286 |
| 2011/0288590 | A1* | 11/2011 | O'Farrell ........... A61B 17/7059 606/264 |
| 2013/0053898 | A1 | 2/2013 | Voisard et al. |
| 2014/0277183 | A1* | 9/2014 | Stalcup ................. A61L 31/146 606/298 |
| 2015/0202046 | A1* | 7/2015 | Whyne ................ A61L 31/127 623/23.62 |

OTHER PUBLICATIONS

Peltoniemi HH, Ahovuo J., Tulamo RM, Tormala PO, Waris T.; Biodegradable and Titanium Plating in Experimental craniotomies: A radiographic follow-up study., Journal of Craniofacial Surgery, 1997; 8(6):446-451.

Serlo W, Kaarela OI, Peltoniemi HH, Merikanto J, Ashammakhi NA, Lassila K, Pohjonen T, Tormala PO, Waris TH; Use of self-reinforced polylactide osteosynthesis devices in craniofacial surgery: A long-term follow-up study. Scandinavian Journal of Plastic and Reconstructive Surgery and Hand Surgery 2001; 35(3):285-292.

International Search Report and Written Opinion, PCT/CA2013/050570, dated Sep. 26, 2013, 5 pages and 4 pages.

* cited by examiner

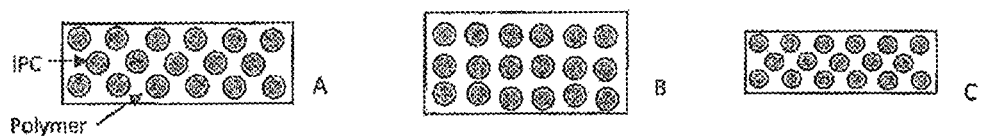
Figure 3: "Bone Tape": Three sheet patterns consisting of potential simple rivet-like design
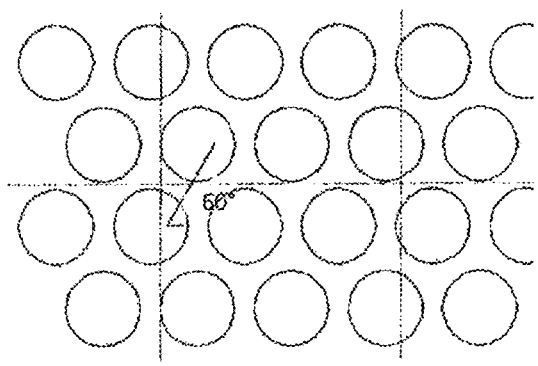
FIGURE 4:
Hexagonal packing arrangement of CPP tabs

BONE STABILIZATION DEVICE AND METHOD OF PRODUCTION

CROSS REFERENCE TO RELATED U.S. PATENT APPLICATION

This patent application is a National Phase application claiming the benefit of PCT/CA2013/050570 filed on Jul. 22, 2013, in English, which further claims priority to U.S. provisional patent application Ser. No. 61/677,290 filed on Jul. 30, 2012 entitled BONE STABILIZATION DEVICE AND METHOD OF PRODUCTION, filed in English, the contents of which are incorporated herein in theft entirety by reference.

FIELD

The present invention relates to a bone stabilization device for use in stabilizing bone fragments, grafts or segments, and to processes for production thereof.

BACKGROUND

Severe traumatic craniomaxillofacial (CMF) fracture commonly occurs due to motor vehicle accidents (including air bag deployment), sports injuries, war injuries and physical assault. One-third of all war injuries are CMF injuries, often involving severe comminution and extensive loss of tissue caused by blast and high velocity mechanisms.[1,2] Traumatic injuries of the CMF skeleton lead to both functional and psychosocial disabilities. Bony reconstructive procedures, such as correction of craniomaxillofacial deformities, through elective osteotomies and bone graft stabilization, also represent complex healing scenarios for CMF skeletal structures.

Successful healing of these injuries and reconstructive procedures relies on accurate reduction and internal stabilization of bone fragments with complex morphologies in 3D space. Current fixation technology is focused on plates and screws, however, this technology is limited to regions of the facial skeleton with sufficient bone density for screw purchase. Furthermore, application of such "hardware" is associated with morbidities related to the hard and soft tissue disruption inherent in the procedure as well as hardware profile.[3] Reported rates of re-operation for CMF hardware removal, for instance, are as high as 50%.[4]

The development of non-metallic thin devices with an initial stiffness close to that of bone (to minimize stress shielding), which can reduce their stiffness through resorption as healing progresses, is a goal of biomaterials research in fracture, graft and osteotomy segment stabilization.[5,6,7] Yet current resorbable hardware is cumbersome with high profiles that are undesirable in many regions of the CMF skeleton, once again limiting sites of application and requiring significant dissection to allow effective application. The ideal fixation technique for the CMF skeleton would therefore be a biocompatible, bioresorbable, low profile system that bonds to the surface of bone, remains flexible enough to allow for semi-stabilized accurate reduction of bone fragments in 3D space at multiple sites, and can then be cured to rigidity to finalize stabilization of the fragments. Furthermore, the ideal fixation device would be translucent in this flexible state, enabling the visualization of fracture lines for more accurate reduction. The absence of this characteristic is another shortcoming of current fixation technologies.

Therefore, it would be beneficial to provide a bone stabilizing implant requiring less bone exposure with an application procedure that creates less tissue destruction than current devices, which can be bonded directly to bone, allows initial semi-stabilized fracture site flexibility, fracture line visualization through the implant if possible, and can be cured to yield a robust construct able to withstand physiologic CMF loading.

SUMMARY

The present disclosure discloses a new innovative device for early bone stabilization, a flexible "bone tape", which may be based on a biodegradable ceramic-polymer interpenetrating phase composite material to treat acute or chronic CMF injuries and deformities and which, after application to bone, can be rigidized to stabilize the site. The concept of a flexible tape represents a paradigm shift in the surgical reconstruction of CMF injuries and deformities beyond plates, screws and glues with multiple advantages for CMF skeletal reconstruction. As in restoration of a shattered vase, the present bone tape allows simultaneous alignment and stabilization of multiple articulated fragments for successful 3D reconstruction. Initial flexibility provided by tape can facilitate the temporary stabilization and alignment adjustment of multiple fragments, prior to permanent rigid bonding.

Thus, there is disclosed a bone stabilization device (also referred to as a bone tape), comprising a composite flexible construct including a rigidifiable biocompatible sheet structure having first and second opposed surfaces and a biocompatible cement located on the first surface. In use, the composite flexible construct is applied to a bone with the cement contacted directly to the bone. The cement is made of a material that, once adhered to the bone, is curable to mechanically and/or ionically bond to the sheet structure and to chemically bond to the bone to achieve a permanent bond.

In an embodiment the bone tape may be constructed of a translucent material so that the translucent quality of the tape allows for accurate fracture alignment, a critical step in the reduction of the small complex fracture and osteotomy segments seen in the CMF skeleton.

As a surface-bonding device, tape is less invasive than fixation hardware (plates, screws, rods, etc.) and is more versatile than the latter in its potential sites of application, thus, decreasing the need for extensive dissection to find adequate bone purchase. The bone tape disclosed herein is not dependent on the thickness or density of bone for stabilization. When an embodiment of the bone tape using translucent material is used, the translucent quality of the tape facilitates accurate fracture and osteotomy site alignment. The flexibility of the tape further allows wrapping and bonding to complex bony contours yielding robust 3D stabilization. As such, the present bone tape may allow for technically easier, more accurate acute facial fracture and osteotomy segment stabilization (particularly for injuries which involve severe comminution and/or bone loss) with less exposure, operative time and consequent morbidity.

A further understanding of the functional and advantageous aspects of the invention can be realized by reference to the following detailed description.

BRIEF DESCRIPTION OF DRAWINGS

The following is a description of the "bone tape" device, reference being had to the accompanying drawings, in which:

Table 1A shows a list of natural candidate polymers that may be used in the bone fixation device disclosed herein;

Figure 1:
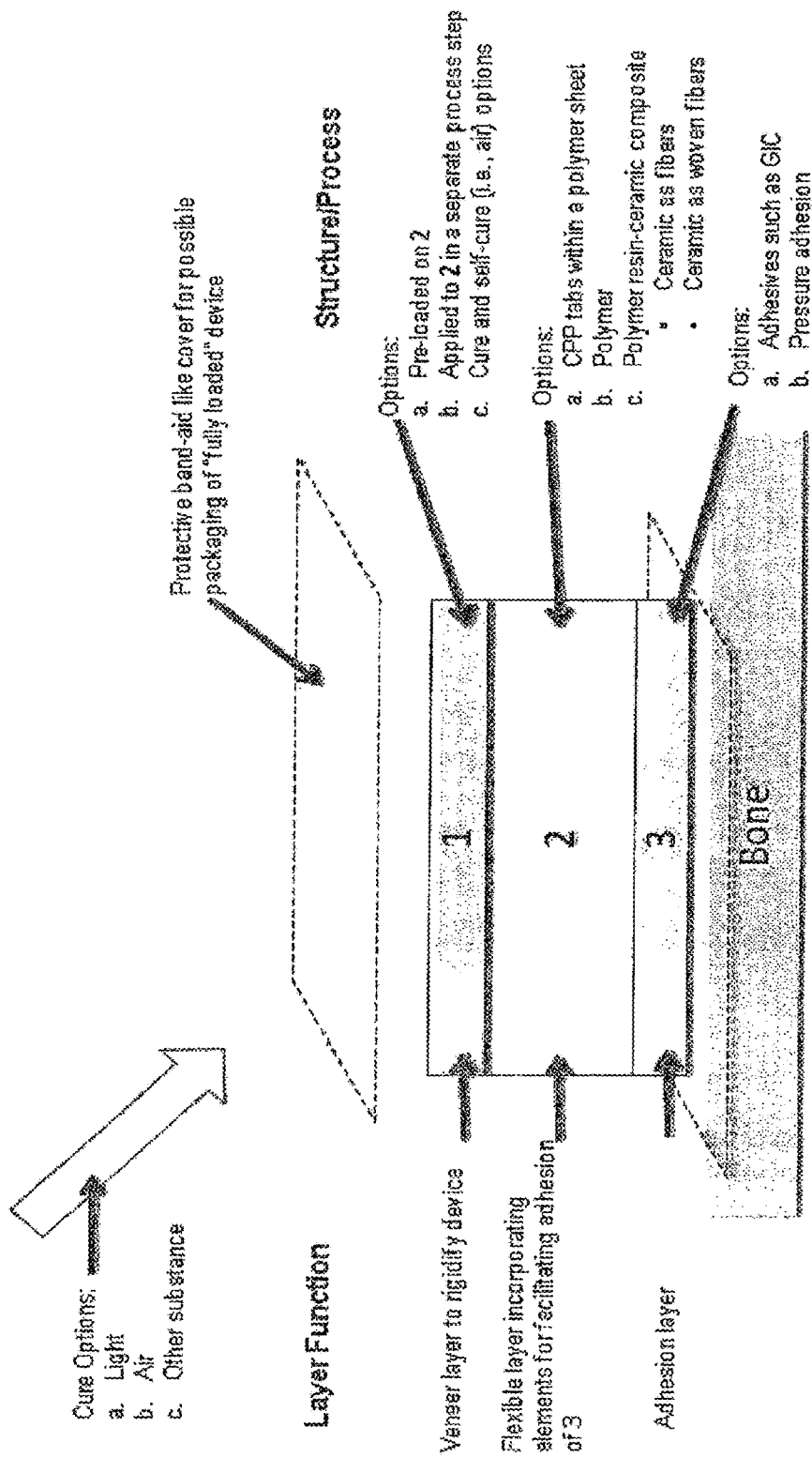
Figure 2:
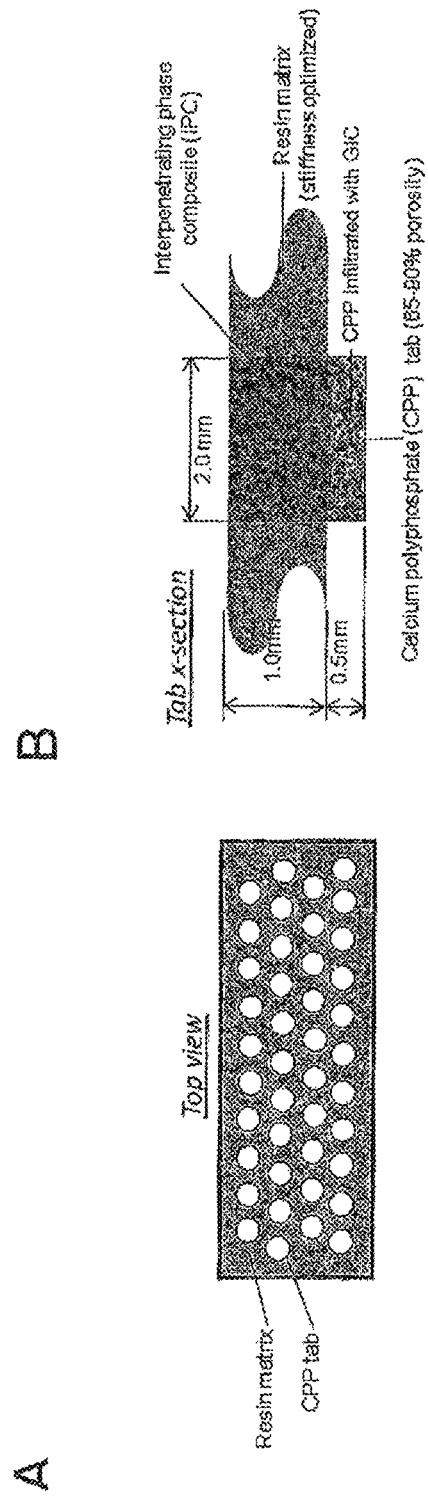

Table 1B shows a list of synthetic candidate polymers that may be used in the bone fixation device disclosed herein;

Table 2 lists the amounts of the resin components used for producing the exemplary flexbile bone tape;

Table 3 lists the exemplary formulas of the veneer solutions that were studied;

FIG. 1 shows a diagrammatic representation of a bone fixation and surgical reconstruction device as disclosed herein;

FIG. 2 shows an embodiment of a sheet pattern consisting of potential simple rivet-like design of IPC tabs embedded in and surrounded by polymer and a cross section of a polymer embedded CPP tab (A: Top view; B: Cross-section of the tab);

FIG. 3 shows three sheet patterns consisting of potential simple rivet-like design for the bone tape disclosed herein;

FIG. 4 shows a detailed view of hexagonal packing arrangement of CPP tabs; and

Figure 5:
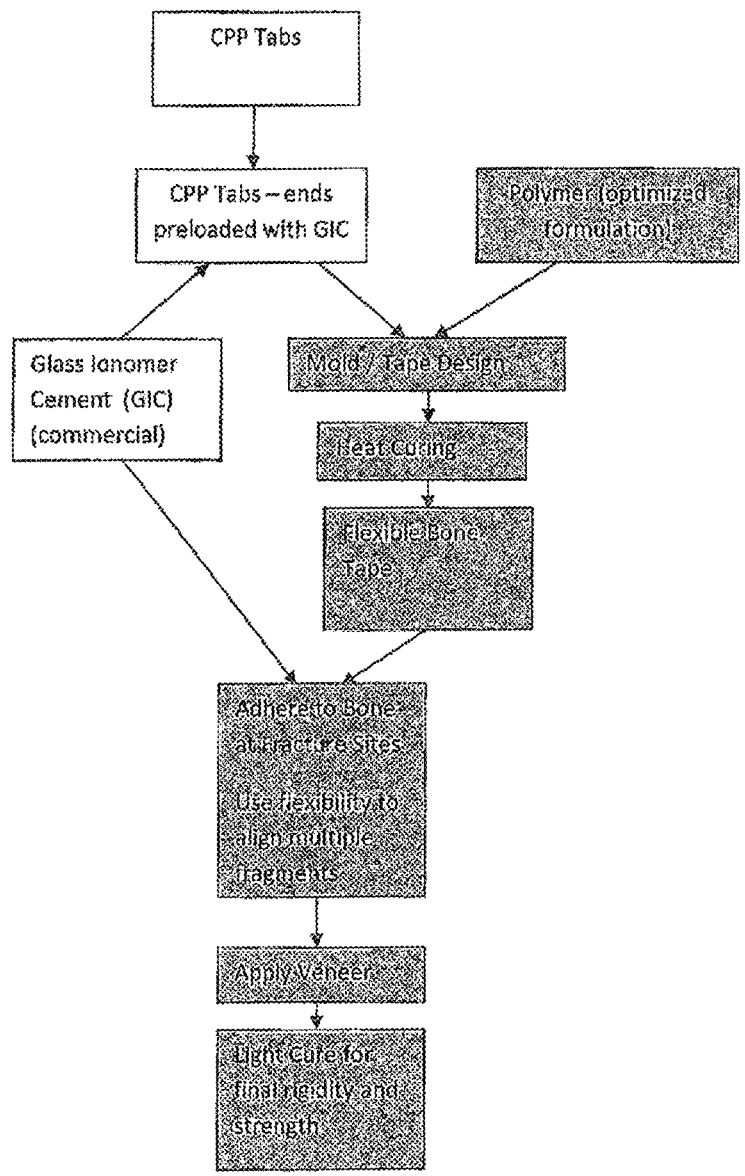

FIG. 5 shows an exemplary process flow diagram for producing the flexible bone fixation device disclosed herein.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

Definitions

As used herein, the terms, "comprises" and "comprising" are to be construed as being inclusive and open ended, and not exclusive. Specifically, when used in this specification including claims, the terms, "comprises" and "comprising" and variations thereof mean the specified features, steps, or components are included. These terms are not to be interpreted to exclude the presence of other features, steps, or components.

As used herein, the term "exemplary" means "serving as an example, instance, or illustration," and should not be construed as preferred or advantageous over other configurations disclosed herein.

As used herein, the terms "about" and "approximately", when used in conjunction with ranges of dimensions of particles, compositions of mixtures, or other physical properties or characteristics, are meant to cover slight variations that may exist in the upper and lower limits of the ranges of dimensions so as to not exclude embodiments where on average most of the dimensions are satisfied but where statistically dimensions may exist outside this region. It is not the intention to exclude embodiments such as these from the present disclosure.

As used herein, the term "flexible" means conformable to the contours of bone and allows for required motion to align multiple fracture sites associated with a given fragment.

As used herein, the term "rigidifiable" means that the stiffness of the construct is increased to a sufficient level to allow fracture healing to occur.

As used herein, the term "cement" means an adhesive/binding element that allows objects to adhere to one another and unites the objects, and in the present context, the purpose of the cement is to withstand physiologic load.

As used herein, the term "curable" means that a material can be changed from its initial state and set to a final form to achieve strong inter-atomic bonding through energy input (i.e. thermal, radiation, chemical, air or light, but not limited to these).

As used herein, the phrase "biologically and physiologically compatible" means the material will have no adverse effects on cells, tissue or function in vivo, or in other words, it is biocompatible.

As used herein, the term "bioresorbable" means once broken down the material will be assimilated over time naturally within the in vivo physiologic environment.

As used herein, the term "biodegradable" means the material is capable of being broken down especially into innocuous products by the action of living things (the in vivo physiologic environment).

As used herein, the phrase "mechanically bond" or "mechanical bond" means a physical interlock (mechanically interlocked) that resists separation by an external force.

As used herein, the phrase "chemically bond" or "chemical bond" means a force that bonds two substances that are brought into close contact (atomic dimensions on the order of angstroms) and the molecules of one substance adhere or are attracted to the molecules of another substance. These interactions are typically covalent or ionic in nature but may include combinations of hydrogen bonding or very strong dipole bonding. An ionic bond refers to a chemical bond formed between oppositely charged species because of their mutual electrostatic attraction between two oppositely charged ions.

An embodiment of a bone stabilization device constructed in accordance with the present disclosure includes a composite flexible construct including a rigidifiable biocompatible sheet structure having first and second opposed surfaces and a biocompatible cement located on the first surface. In use, the composite flexible construct is applied to a bone with the cement contacted directly to the bone. The cement is made of a material that, once adhered to the bone, is curable to mechanically and/or ionically bond to the sheet structure and to chemically bond to the bone to achieve a permanent bond.

In an embodiment a main constituent of said biocompatible sheet structure is a biodegradable and/or bioresorbable polymer material. The polymer material is comprised of a polymer containing repeating groups which include any one or a combination of amides, peptides, urethanes, esters, carbonates, anhydrides, ethers, and sulphonamides. Tables 1A and 1B show lists of natural and synthetic candidate polymers that may be used.

The biocompatible sheet structure includes a plurality of separate designated bonding sites to form a plurality of bonds between the composite flexible construct and the bone. The separate designated bonding sites may include pores extending through the biocompatible sheet structure so that the cement fills the pores and can flow onto the second surface of the sheet to form a strong bond to the sheet and the bone. Alternatively, the separate designated bonding sites may include open porous regions of the polymer material which are filled with the cement to form the bonding sites.

The composite flexible construct may further include a porous, biocompatible, biodegradable and bioresorbable material such that the composite flexible construct is a porous bioresorbable material composite. In an embodiment this composite may contain a porous ceramic. The porous ceramic may be any one or combination of calcium polyphosphate (CPP), tricalcium polyphosphate, mixed calcium phosphate, and calcium sulphate-calcium phosphate mixtures. The mixed calcium phosphate may be any one or combination of tricalcium phosphate and calcium hydroxyapatite. In an embodiment, the porous ceramic is calcium polyphosphate with additive cations that substitute for Ca ions. The additive cations that substitute for Ca ions may be any one or combination of Si and Na.

The porous ceramic may be a mesh formed from calcium phosphate-based biodegradable and biocompatible ceramic fibers, the ceramic fibers being any one of calcium polyphosphate, tricalcium phosphate, and calcium sulphate-calcium phosphate mixtures. These ceramic fibers may be multidirectional fibers having a length sufficiently long to form a random mesh arrangement with openings for cement and polymer intrusion.

In another embodiment, the bioresorbable structures may be flexible bioresorbable structures. For example, the porous biocompatible, biodegradable and bioresorbable material may include biocompatible, biodegradable and bioresorbable polymer fibers in a biocompatible, biodegradable and bioresorbable polymer resin. These porous materials may include an open weave of biocompatible and biodegradable fibers.

The fibers may also be ceramic fibers (multidirectional short fibres or longer uni- or bi-directional fibers). They may be woven fibers (CPP or polymer) in a polymer resin. Alternatively they may be an open weave of fibers which bonds to bone via glass ionomer cement (GIC) infiltration. Following reconstruction, the midsection of the open weave can be filled with GIC or other substance to achieve rigidity, a key being that the constituents are selected to ensure the fibers are strongly bonded to the bone.

The porous biocompatible, biodegradable and bioresorbable material may include a plurality of rigid bioresorbable structures, and may be biodegradable inorganic structures or organic biodegradable structures. The inorganic structures may be metallic structures or structures are ceramic structures, such as but not limited to calcium polyphosphate structures. The rigid bioresorbable structures have a cross sectional shape which is any one or combination of cylindrical, rectangular, square, triangular, and star-shaped blocks.

The bioresorbable structures may be arranged in a preselected periodic repeating pattern along the polymer sheet structure in such a way as to give the resulting flexible tape the ability to twist, flex and conform to uneven/irregular geometries. This flexibility allows contouring to bone thus facilitating binding and fixing complex reconstruction of multiple bone fragments not amenable to the traditional mechanical fixturing requiring plates, rods and screws.

The structures can be laid out in periodic patterns with the structures spaced from each other such that the resulting polymer-structure composite is flexible and can be twisted and flexed in specific ways to be applied to irregular shaped bones. A long tape can be produced with multiple sections of patterns spaced from each other so that the tape can be cut up into desired lengths by the surgeon applying the tape to the patient's broken bones.

Preferably, the rigid bioresorbable structures are porous ceramic (most preferably CPP) have first sections that are penetrated by polymer (or monomer of the polymer) of which the sheet structure is made thus forming a polymer-bioresorbable structure composite, and second sections that are penetrated by the cement for binding the bioresorbable structures to the bone.

As mentioned above, a preferred rigid porous ceramic material is porous CPP structures, but other porous materials could be used. For example metal Mg-based alloys may be used such as those disclosed by Julie Le'vesque, Hendra Hermawan, Dominique Dube', Diego Mantovani, "Design of a pseudo-physiological test bench specific to the development of biodegradable metallic biomaterials"; J. Le'vesque et al./Acta Biomaterialia 4 (2008) 284-295.

A preferred rigid bioresorbable biodegradable inorganic structure is a porous ceramic material having a porosity of the first section embedded in the polymer sheet such that the monomer of the flexible polymer sheet in which the structures are embedded can flow into the porous first section so that when the polymer-ceramic composite is cured the polymer polymerizes within the porous first sections of the rigid bioresorbable structures. The second porous section of the structure has a porosity sufficient so that a cement can flow into the second section to bind the second section to bone, polymer (or more particularly monomer of the polymer) can flow into the first section and will be controlled to prevent its entry to the second section thereby allowing retention of the cement infused porous structure of the second section.

An advantage of using a polymer-ceramic composite (2 phases) allows fine-tuning of mechanical properties. This embodiment may be configured as a veneer-polymer-ceramic (CPP) composite and may be produced utilizing multiple unidirectional pieces of tape. The bone tape is configured to provide sufficient interface shear strength (failure at the cement—bone interface).

The present bone stabilization device, also referred to as bone tape, exhibits several advantageous features. It is designed to be flexible and cures to rigidity once applied. In an embodiment the bone tape may be produced of a material that is translucent to allow for visualization of fracture reduction by the surgeon. The tape can be made of varying dimensions, length, width and thickness depending on the bone structures being stabilized, and the amount of loading anticipated on that site.

In embodiments the bone tape is produced of materials that adhere in wet environments and remains adherent in both the flexible and rigid state. The tape can be trimmed, cut to any size or shape (or produced in multiple shapes/sizes), and has the needed flexibility and thinness to allow for complete conformity to any bone contour. The strength of the tape and its bond to bone is adequate to withstand loading that occurs under manipulation during reduction of bone.

The sheet structure preferably includes at least an oligomer containing degradable moieties, for example the oligomer may include (but is not restricted to) divinyl oligomer. The sheet structure may be made from vinyl monomers including hydroxyethylmethacrylate, methylmethacrylate and ethylmethacrylate. The degradable moieties may include any one or combination of polycarbonate and polyester, polyamide or polypeptide and polysulfonamide.

Referring to FIG. 1, all of the embodiments above of the bone stabilization device may include a veneer layer 1 located on the second surface of the flexible layer 2 which has located on its first surface a cement layer 3 to produce a modified biocompatible sheet structure. The resulting modified biocompatible sheet structure 1/2/3 has a higher stiffness than the biocompatible sheet structure due to the veneer being made of a material that is curable to stiffen the modified biocompatible sheet structure. The veneer may be any one or combination of poly(D,L-lactide-co-glycolide), polycarbonates, poly(glycolide), poly(glycolic acid-co-l- lactic acid), poly(l-lactide), poly(l-lactic acid-co-e-caprolactone), poly(e-caprolactone), poly(p-dioxanone), and poly (orthoester).

The poly(D,L-lactide-co-glycolide) polymer preferably has a composition in a range of about 5% to about 95% lactide relative to glycolide, and has a molecular weight in a range from about 10,000 to about 200,000 Daltons (Da). The veneer may contain a degradable polymer that is any one or combination of biodegradable polyesters, polyanhydrides, polycarbonates, polyurethanes, starch derivatives, cellulose esters and combinations of these.

The biodegradable polyesters may be a naturally produced aliphatic polyester, an aliphatic polyester of a renewable resource and a synthetic aliphatic polyester. Preferably the naturally produced aliphatic polyester is a polyhydroxyalkanoate (PHA), including poly-3-hydroxybutyrate (PHB), polyhydroxyvalerate (PHV) and polyhydroxyhexanoate (PHH). The aliphatic polyester of renewable resource may be polylactic acid (PLA) or polyglycolic acid. The synthetic aliphatic polyester may be polybutylene succinate (PBS) or polycaprolactone (PCL). The cellulose esters may be cellulose acetate, nitrocellulose and their derivatives, and the cellulose derivatives may be celluloid.

In any of the embodiments disclosed above, the cement may be any one or combination of glass ionomer cements, resin-modified glass ionomer cements and cyanoacrylate cements.

An alternative to using a veneer as disclosed above, it will be appreciated by those skilled in the art that a polymer material may be used that is curable, once the cement is adhered to the bone, to achieve a rigid final form. In very low loading scenarios (as found in communited cranial fractures for example), the bone tape may be applied as a sheet over multiple aligned fragments, providing adequate stabilization without additional veneer or curing.

When veneer is used, it may be applied to the back side of the bone tape after the fragments have been aligned and the tape has been applied to bone, or it may be in a "ready-to-use" configuration in which it is integrated as a layer on the initial tape during production thereof and protected by a protective covering that can be peeled off when it is time to rigidize the device. The selected veneer is biocompatible and biodegradable.

When a veneer is used, the polymer material forming the main constituent of the biocompatible sheet structure should satisfy the following set of functions, including being biocompatible, bioresorbable, optimized initial flexibility/ strength, not too rigid, but with some substance and somewhat more rigid than duct tape, clear so the surgeon can see through to the bone.

The present invention will now be illustrated with the following non-limiting Examples, which are to be understood as being purely exemplary and not limiting the invention in any way.

Example 1

An example of a "bone tape" composite material of ceramic-polymer interpenetrating phase composite (IPC) tabs distributed within a polymer sheet in a rivet-like pattern was made. An interpenetrating phase composite (IPC) resin (CPP infiltrate) was prepared by uniformly mixing divinyl polycarbonate urethane (DVO), ethyl methacrylate (EMA), polytetramethylene oxide (PTMO) and benzoyl peroxide (BPO) in a glass vial. This solution was kept at ~4° C. until used. Table 2 lists the amounts of the resin components. For sample curing, an oven with a slow nitrogen flow was heated to 110° C. for 30 min. The resin solution was warmed at room temperature for 30 minutes and placed in the oven. The nitrogen flow was sustained for 10 min and then was shut down. The curing continued at 110~115° C. for 48 hours. The components of the resin solution were varied as per Table 2 to alter the flexibility/modulus of the resin. Lower amounts of plasticizer will infiltrate the CPP tabs easier. R24 (see Table 2) was determined to best represent the clinical "feel" desired for the initial pre-cured bone tape and was utilized for further tape development. It was found that this optimized resin was taken up into the CPP tabs (60% to 90% dense) and was able to cure into a bone tape material.

Several designs were investigated for the layout of the CPP rivets within the polymer tape to allow bonding to curved/uneven bony surfaces, while retaining the maximum bonding surface area. Analytic calculations were used to determine the maximum flex angles possible with each configuration (based on diameter, height and pitch spacing/ packing density). It was determined that for a given maximum permissible bending angle (as determined by pitch spacing), a lower tab thickness to CPP tab diameter will provide the greater adhesion shear strength in the overall tape. In addition, better flexibility is possible with a greater number of smaller tabs. The ability to fabricate smaller diameter CPP tabs allowed for such a design to be feasible. As such, an embodiment of the design utilizes 2 mm diameter CPP tabs (height 1.5 mm, 70% density) arranged as per FIG. 2A. The hexagonal packing of these tabs yield a CPP surface area of ~60%, delivering the desired bonding strength. The flexibility of this design will allow bending at >45 degrees. Fabrication of the composite was achieved using a tape casting process.

Optimal Bonding Protocol to Adhere the "Bone Tape" Implant to CMF Bone Using GICs.

To evaluate the ability of GICs to adhere the interpenetrated CPP tabs to CMF bone specimens (1×2 cm strips) mechanical testing was conducted to assess the implant-bone shear strength of the bonded material. Single CPP tabs (4.5 mm diameter) were attached to the outer surface of human cortical bone samples using glass ionomer cement (GIC). A Fuji GIC was used following pre-treatment of the bone and CPP surface with a Ketak conditioner (polyacrylic acid). The Ketak GIC was deemed too viscous for this application. Application of the GIC was as per manufacturers guidelines. Each bone-GIC-CPP tab construct was set-up in the MTS Bionix 858 servohydraulic testing system within a custom-made fixture. The bone was fixed in PMMA cement. The construct was loaded in shear until failure (rate 0.01 mm/s). Testing was conducted on individual CPP rivets as described above.

In all samples, the shear failure resulted with the detachment of the GIC bond from the bone. There were no mechanical failures in any of the CPP tabs. From post-test visual inspection it was clear that the GIC layer was lifted entirely from the bone surface, while still adhering to the CPP tab. The shear failure load was 20-30N in all samples. Similar results were found with both IPC-infiltrated and non-infiltrated CPP tabs. This shear strength falls within the ranges reported for commercially available GICs. It was found that GIC was able to bond to infiltrated CPP tabs and as such this represents the easiest scenario.

The current design has GIC surrounding the bottom of the CPP tab, which likely gives added shear stability to the construct. As such designing a tab with the CPP tabs sticking out below the Tape (Polymer) is a design benefit. The bone-GIC interface strength of the infiltrated CPP tabs and was found to be in line with the estimated shear strength requirements. The size and number of tabs and the GIC coverage area will determine the overall shear strength of each construct. FIG. 3 shows three sheet patterns consisting of potential simple rivet-like design for the bone tape disclosed herein.

A packing area density criterion, which is a measure of CPP surface area per unit area of the tape, was used to optimize the pattern of CPP tab placement. The geometrical arrangement chosen was a hexagonal pattern, which displaces each tab at a 60 degrees off-axis to its closest neighbor (FIG. 4 shows a detailed view of hexagonal packing arrangement of CPP tabs). This pattern has three distinct advantages compared to simple Cartesian or other staggered patterns. First, in quantitative geometrical terms, hexagonal packing provides the highest density of circular objects attainable in any space. Second, this pattern is isotropic in the 2-dimensional plane of the tape, which provides the same degree of flexibility in all directions. Finally, the tape placed on any arbitrary 3-dimensional curved topology will have the most even and uniform distribution of CPP tabs over that area.

Process to Cure the "Bone Tape" Construct.

Divinyl crosslinker (HLH), poly(D,L-lactide-co-glycolide) (PLGA), methyl methacrylate (MMA) and photosensitive initiator made of camphorquinone (CQ) and 2-(dimethylamino)ethyl methacrylate (DMAEMA) were mixed for 12 h with a small volume of $CH_2Cl_2$ added to help the mixture to form a homogeneous solution. Table 3 lists the formulas of the veneer solutions that were tried. The solution was cast on a Teflon or a glass surface in a dark environment. After evaporating the solvent, the viscous glue-like solid was collected, covered with a piece of glass and pressed. The curing was photo-initiated by a dental blue light (max 420 mW/$cm^2$) for 2×30 seconds by using a model Optilux 501 light source (sds Kerr, U S). The cured solid veneer samples were easy to remove from Teflon surface, but needed to be cut from glass surface carefully.

The veneers with PLGA (75:25) as the filler (V8 and V9) were found be too soft; the veneers with PLGA (50:50) as the filler (V10 and V12) were found be too brittle. To overcome those problems, we made samples with mixtures of different ratios of PLGA (75:25) and PLGA (50:50).

Both the molecular weight and the PL/PG ratio of PLGA were found to be important parameters influencing the physical properties of the veneers (i.e. higher molecular weight PLGAs were used to overcome problems with brittleness). The veneers (V21 and V24) made with PLGA (65:35, Mw 40 kD-75 kD) were found to have a moderate hardness and strength. We further combined the V24 and V29 formulations with CPP powder (<25µ grain size) at 5, 10, 20 and 30% bt weight. To obtain a uniform blending of the inorganic CPP powder to the organic veneer solution, the viscous dough was kneaded (folded and pressed) repeatedly (×50) on a Teflon board. The material was pressed between two pieces of glass and photocured. The resultant samples were uniform, without bubbles and strengthened.

FIG. 5 shows an exemplary process flow diagram for a method of producing the IPC structure discussed above.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

REFERENCES

1. Dobson J E, Newell M J, Shepherd J P. Trends in maxillofacial injuries in war-time (1914-1986). Br J Oral Maxillofac Surg. 1989; 27:441-450.
2. Ringler D, Einy S, Giveon A, Goldstein L, Peleg K. Maxillofacial trauma resulting from terror in Israel. J Craniofac Surg. 2007; 18(1):62-66.
3. Regev E, Shiff J S, Kiss A, Fialkov J A. Internal fixation of mandibular angle fractures: a meta-analysis. Plastic and Reconstructive Surgery (2010) 125(6):1753-60.
4. Nagase D Y, Courtemanche D J, Peters D A. Plate removal in traumatic facial fractures. 13 year practice review. Ann Plast Surg. 2005; 55:608-611.
5. Pietrzak W S, Sarver D, Verstynen M. Bioresorbable implants—Practical considerations. Bone 1996; 19(1): 109-119.
6. Peltoniemi H H, Ahovuo J, Tulamo R M, Tormala P O, Waris T. Biodegradable and titanium plating in experimental craniotomies: A radiographic follow-up study. Journal of Craniofacial Surgery 1997; 8(6):446-451.
7. Serlo W, Kaarela O I, Peltoniemi H H, Merikanto J, Asharnmakhi N A, Lassila K, Pohjonen T, Tormala P O, Waris T H. Use of self-reinforced polylactide osteosynthesis devices in craniofacial surgery: A long-term follow-up study. Scandinavian Journal of Plastic and Reconstructive Surgery and Hand Surgery 2001; 35(3):285-292.

TABLE 1A

Classification of biodegradable natural polymers

| Sub-classification | Examples |
| --- | --- |
| 1. Plant origin | |
| 1.1 Polysaccharides | Cellulose |
| | Starch |
| | Alginate |
| 2. Animal origin | |
| 2.1 Polysaccharides | Chitin (Chitosan) |
| | Hyaluronate |
| 2.2 Proteins | Collagen (Gelatin) |
| | Albumin |
| 3. Microbe origin | |
| 3.1 Polyesters | Poly(3-hydroxyalkanoate) |
| 3.2 Polysaccharides | Hyaluronate |

TABLE 1B

Classification of biodegradable synthetic polymers

| Sub-classification | Examples |
| --- | --- |
| 1. Aliphatic polyesters | |
| 1.1 Glycol and dicarbonic acid polycondensates | Poly(ethylene succinate) Poly(butylenes terephthalate) |
| 1.2 Polylactides | Polyglycolide, Polylactides |
| 1.3 Polylactones | Poly(e-carpolactone) |
| 1.4 Miscellaneous | Poly(butylenes terephthalate) |
| 2. Polyols | Poly(vinyl alcohol) |
| 3. Polycarbonates | Poly(ester carbonate) |
| 4. Miscellaneous | Polyanhydrides, Poly(a-cyanoacrylate)s Polyphosphazenes Poly(orthoesters) |

TABLE 2

Materials used for preparing the resin solutions for the IPC

| | DVO | | | EMA | | | PTMO1000 | | BPO | | |
|---|---|---|---|---|---|---|---|---|---|---|---|
| | mg | mmol | wt % | mg | mmol | wt % | mg | wt % | mg | μmol | wt % |
| R 3 | 161.1 | 0.1 | 77.81 | 45.6 | 4.0 | 22.040 | | | 0.3 | 1.26 | 0.145 |
| R 16 | 161.1 | 0.1 | 77.07 | 45.6 | 4.0 | 21.829 | 2.0 | 0.957 | 0.3 | 1.26 | 6.145 |
| R 22 | 161.1 | 0.1 | 77.74 | 45.6 | 4.0 | 22.019 | 0.2 | 0.097 | 0.3 | 1.26 | 0.145 |
| R 23 | 80.6 | 0.05 | 77.82 | 22.8 | 2.0 | 22.028 | 0.01 | 0.010 | 0.15 | 0.63 | 0.145 |
| R 24 | 805.5 | 0.50 | 77.81 | 228.15 | 20.0 | 22.04 | 0.01 | 0.001 | 1.50 | 12.6 | 0.145 |
| R 25 | 1611.0 | 1.00 | 77.07 | 456.30 | 40.0 | 21.83 | 20.00 | 0.957 | 3.00 | 12.60 | 0.144 |

TABLE 3

Materials used for preparing solutions for the light cure veneer

| | HLH | | | MMA | | | | | CQ + DMAEMA mol/mol = 1/2 | | $CH_2Cl_2$ | Total | L:G | Mw av |
|---|---|---|---|---|---|---|---|---|---|---|---|---|---|---|
| | mg | μmol | wt % | mg | μmol | wt % | mg | wt % | mg | wt % | ml | % | % | kD |
| | | | | | | | PLGA (75:25) Mw 66k~107k | | PLGA (50:50) Mw 7k~17k | | | | | |
| V 8 | 25 | 105.8 | 21.99 | 25 | 290 | 21.99 | 56.20 | 49.42 | 0 | 0.00 | 7.51 | 6.61 | 0.1 | 75 | 25 | 86.5 |
| V 9 | 4 | 16.93 | 3.91 | 15 | 174 | 14.66 | 82.00 | 80.14 | 0 | 0.00 | 1.33 | 1.30 | 0.2 | 75 | 25 | 86.5 |
| V 10 | 4 | 16.93 | 3.91 | 15 | 174 | 14.66 | 0 | 0 | 82 | 80.14 | 1.33 | 1.30 | 0 | 50 | 50 | 12 |
| V 11 | 5.3 | 22.4 | 5.00 | 15 | 174 | 14.66 | 0 | 0 | 83 | | 2.65 | | 0.2 | 50 | 50 | 12 |
| V 12 | 5.3 | 22.4 | 5.00 | 15 | 174 | 14.16 | 0 | 0 | 83 | 78.34 | 2.65 | 2.50 | 0.2 | 50 | 50 | 12 |
| V 13 | 5.3 | 22.4 | 4.82 | 15 | 174 | 13.64 | 87.00 | 79.13 | 0 | 0.00 | 2.65 | 2.41 | 0.2 | 75 | 25 | 86.5 |
| V 14 | 5.3 | 22.4 | 5.00 | 15 | 174 | 14.16 | 42.85 | 40.44 | 40.15 | 37.89 | 2.65 | 2.50 | 0.2 | 62.91 | 37.09 | 39.53 |
| V 15 | 5.3 | 22.4 | 5.00 | 15 | 174 | 14.16 | 20.52 | 19.37 | 62.48 | 58.97 | 2.65 | 2.50 | 0.2 | 56.18 | 43.82 | 23.83 |
| V 17 | 2.6 | 11.2 | 5.01 | 7.5 | 87 | 14.81 | 20.82 | 40.57 | 19.00 | 37.02 | 1.33 | 2.59 | 0.1 | 63.07 | 36.93 | 39.53 |
| V 18 | 5.3 | 22.4 | 5.00 | 15 | 174 | 14.15 | 83.00 | 78.30 | 0 | 0.00 | 2.70 | 2.55 | 0.2 | 75 | 25 | 86.5 |
| V 19 | 5.3 | 22.4 | 5.00 | 15 | 174 | 14.15 | 42.85 | 40.42 | 40.15 | 37.88 | 2.70 | 2.55 | 0.2 | 62.91 | 37.09 | 39.51 |
| V 20 | 5.3 | 22.4 | 5.00 | 15 | 174 | 14.15 | 20.52 | 19.36 | 62.48 | 58.94 | 2.70 | 2.55 | 0.2 | 56.18 | 43.82 | 23.82 |
| V 25 | 2.65 | 22.4 | 5.00 | 7.5 | 174 | 14.15 | 41.50 | 78.30 | 0 | 0 | 1.35 | 2.55 | 0.1 | 75 | 25 | 86.50 |
| V 26 | 2.65 | 22.4 | 5.00 | 7.5 | 174 | 14.15 | 20.75 | 39.15 | 20.75 | 39.15 | 1.35 | 2.55 | 0.1 | 62.5 | 37.5 | 38.56 |
| | | | | | | | PLGA (65:35) Mw 40k~75k | | | | | | | |
| V 21 | 5.3 | 22.4 | 5.00 | 15 | 174 | 14.15 | 0 | 0 | 83.00 | 78.30 | 2.70 | 2.55 | 0.2 | 65 | 35 | 57.50 |
| V 24 | 5.3 | 22.4 | 5.00 | 15 | 174 | 14.15 | 0 | 0 | 83.00 | 78.30 | 2.70 | 2.55 | 0.15 | 65 | 35 | 57.50 |
| | | | | | | | PLGA (65:35) Mw 24k~38k | | | | | | | |
| V 27 | 5.3 | 22.4 | 5.00 | 15 | 174 | 14.15 | 0 | 0 | 83.00 | 78.30 | 2.70 | 2.55 | 0.08 | 65 | 35 | 31.00 |
| | | | | | | | PLGA (50:50) Mw 38k~54k | | | | | | | |
| V 28 | 5.3 | 22.4 | 5.00 | 15 | 174 | 14.15 | 0 | 0 | 83.00 | 78.30 | 2.70 | 2.55 | 0.08 | 50 | 50 | 46.00 |
| | | | | | | | PLGA (75:25) Mw 76k~115k | | <25 μm CPP | | | | | |
| V 29 | 5.3 | 22.4 | 5.00 | 15 | 174 | 14.15 | 83.00 | 78.30 | 0 | 0 | 2.70 | 2.55 | 0.08 | 75 | 25 | 95.50 |
| V 30* | 5.3 | 22.4 | 4.75 | 15 | 174 | 13.44 | 83.00 | 78.30 | 5.58 | 5.00 | 2.70 | 2.42 | 0.08 | 75 | 25 | 95.50 |
| V 31* | 5.3 | 22.4 | 4.50 | 15 | 174 | 12.74 | 83.00 | 78.30 | 11.78 | 10.00 | 2.70 | 2.29 | 0.08 | 75 | 25 | 95.50 |
| V 32* | 5.3 | 22.4 | 4.00 | 15 | 174 | 11.32 | 83.00 | 78.30 | 26.50 | 20.00 | 2.70 | 2.04 | 0.08 | 75 | 25 | 95.50 |
| V 33* | 5.3 | 22.4 | 3.50 | 15 | 174 | 9.91 | 83.00 | 78.30 | 45.43 | 30.00 | 2.70 | 1.78 | 0.08 | 75 | 25 | 95.50 |

TABLE 3-continued

Materials used for preparing solutions for the light cure veneer

| | HLH | | | MMA | | | | | | | CQ + DMAEMA mol/mol = 1/2 | | CH₂Cl₂ | Total | L:G | Mw av |
|---|---|---|---|---|---|---|---|---|---|---|---|---|---|---|---|---|
| | mg | μmol | wt % | mg | μmol | wt % | mg | wt % | mg | wt % | mg | wt % | ml | % | % | kD |
| | | | | | | | PLGA (65:35) Mw 40k~75k | | | | | | | | | |
| V 34* | 5.3 | 22.4 | 4.75 | 15 | 174 | 13.44 | 83.00 | 74.39 | 5.58 | 5.00 | 2.70 | 2.42 | 0.15 | 65 | 35 | 57.50 |
| V 35* | 5.3 | 22.4 | 4.48 | 15 | 174 | 12.67 | 83.60 | 70.62 | 11.78 | 10.00 | 2.70 | 2.28 | 0.15 | 65 | 35 | 57.50 |
| V 36* | 5.3 | 22.4 | 3.98 | 15 | 174 | 11.26 | 83.69 | 62.84 | 26.50 | 20.00 | 2.70 | 2.03 | 0.15 | 65 | 35 | 57.50 |
| V 37* | 5.3 | 22.4 | 3.38 | 15 | 174 | 9.85 | 83.89 | 55.08 | 45.43 | 30.00 | 2.70 | 1.77 | 0.15 | 65 | 35 | 57.50 |

What is claimed is:

1. A bone tape, comprising:
a composite flexible construct including
a flexible rigidifiable biocompatible sheet structure having first and second opposed surfaces,
a biocompatible cement located on said first surface,
said cement being made of a material that, once said first surface is adhered to bone, forms a permanent bond, and
wherein the bone tape has flexibility to allow for alignment and stabilization of multiple bone fragments prior to the flexible rigidifiable biocompatible sheet structure being rigidized, and when rigid, acts to hold the bone fragments fixed with respect to each other.

2. The bone tape according to claim 1 wherein a main constituent of said biocompatible sheet structure is a biodegradable and/or bioresorbable polymer material.

3. The bone tape according to claim 2 wherein said biocompatible sheet structure includes a plurality of separate designated bonding sites to form a plurality of bonds between said composite flexible construct and the bone.

4. The bone tape according to claim 3 wherein said separate designated bonding sites include pores extending through said biocompatible sheet structure, and wherein said cement fills said pores.

5. The bone tape according to claim 3 wherein said separate designated bonding sites include open porous regions of the polymer material which are filled with said cement to form a plurality of bonding sites.

6. The bone tape according to claim 2 wherein said composite flexible construct further comprises a porous biocompatible, biodegradable and bioresorbable material such that said composite flexible construct is a porous bioresorbable material composite.

7. The bone tape according to claim 6 wherein said porous biocompatible, biodegradable and bioresorbable material contains a porous ceramic.

8. The bone tape according to claim 7 wherein said porous ceramic is selected from the group consisting of calcium polyphosphate, tricalcium polyphosphate, mixed calcium phosphate, and calcium sulphate-calcium phosphate mixtures.

9. The bone tape according to claim 6 wherein said porous biocompatible, biodegradable and bioresorbable material includes a plurality of rigid bioresorbable structures.

10. The bone tape according to claim 9 wherein said rigid bioresorbable structures are any one of biodegradable inorganic structures and organic biodegradable structures.

11. The bone tape according to claim 10 wherein said inorganic structures are ceramic structures.

12. The bone tape according to claim 11 wherein said ceramic structures are calcium polyphosphate structures.

13. The bone tape according to claim 9 wherein said rigid bioresorbable structures are arranged in a pre-selected periodic repeating pattern along said biodegradable and/or bioresorbable polymer material.

14. The bone tape according to claim 9 wherein said rigid bioresorbable structures have
first sections that are penetrated by polymer of which the sheet structure is made thus forming a polymer-bioresorbable structure composite, and
second sections that are penetrated by the cement for binding the bioresorbable structures to the bone.

15. The bone tape according to claim 14 wherein said sheet structure includes at least an oligomer containing degradable moieties.

16. The bone tape according to claim 1 including a veneer on the second surface to produce a modified biocompatible sheet structure, wherein said modified biocompatible sheet structure has a higher stiffness than the biocompatible sheet structure by said veneer being made of a material that is curable to stiffen the modified polymer sheet structure.

17. The bone tape according to claim 16 wherein said veneer comprises any one or combination of poly(D,L-lactide-co-glycolide), polycarbonates, poly(glycolide), poly(glycolic acid-co-l-lactic acid), poly(I-lactide), poly(l-lactic acid-co-e-caprolactone), poly(e-caprolactone), poly(p-dioxanone), and poly(orthoester).

18. The bone tape according to claim 17 wherein said poly(D,L-lactide-co-glycolide) polymer has a composition in a range of 5% to 95% lactide relative to glycolide, and has a molecular weight in a range from 10,000 to 200,000 Daltons.

19. The bone tape according to claim 1 wherein said cement is any one or combination of glass ionomer cements, resin-modified glass ionomer cements and cyanoacrylate cements.

20. The bone tape according to claim 1 wherein said rigidifiable biocompatible sheet structure is made of a translucent material.

* * * * *

UNITED STATES PATENT AND TRADEMARK OFFICE
CERTIFICATE OF CORRECTION

PATENT NO. : 10,045,801 B2
APPLICATION NO. : 14/418707
DATED : August 14, 2018
INVENTOR(S) : Whyne et al.

It is certified that error appears in the above-identified patent and that said Letters Patent is hereby corrected as shown below:

In the Specification

Column 1, Line 15, INSERT:
--GOVERNMENT LICENSE RIGHTS
This invention was made with government support under Grant Award Number W81XWH-10-1-0995 awarded by US Army Medical Materiel Agency (USAMMA). The government has certain rights in the invention.--

Signed and Sealed this
Twenty-sixth Day of March, 2019

Andrei Iancu
*Director of the United States Patent and Trademark Office*